US006818771B1

(12) United States Patent
Hayes et al.

(10) Patent No.: US 6,818,771 B1
(45) Date of Patent: Nov. 16, 2004

(54) PROCESS FOR THE PRODUCTION OF A NAPHTHYRIDINE CARBOXYLIC ACID DERIVATIVE (METHANESULFONATE SESQUIHYDRATE)

(75) Inventors: Jerome Francis Hayes, Tonbridge (GB); Timothy Charles Walsgrove, Tunbridge Wells (GB); Andrew Stephen Wells, Quorn (GB)

(73) Assignee: LG Life Sciences Limited, Seoul (KR)

( * ) Notice: Subject to any disclaimer, the term of this patent is extended or adjusted under 35 U.S.C. 154(b) by 0 days.

(21) Appl. No.: 09/787,256

(22) PCT Filed: Sep. 15, 1999

(86) PCT No.: PCT/EP99/07003

§ 371 (c)(1),
(2), (4) Date: May 16, 2001

(87) PCT Pub. No.: WO00/17199

PCT Pub. Date: Mar. 30, 2000

(30) Foreign Application Priority Data

Sep. 18, 1998 (GB) ............................................. 9820405

(51) Int. Cl.$^7$ ........................................... C07D 471/04
(52) U.S. Cl. ........................................................ 546/123
(58) Field of Search ............................................. 546/123

(56) References Cited

U.S. PATENT DOCUMENTS

| 5,633,262 A | 5/1997 | Hong et al. | 546/123 |
|---|---|---|---|
| 5,776,944 A | 7/1998 | Hong et al. | 546/123 |
| 5,869,670 A | 2/1999 | Hong et al. | 546/123 |
| 5,962,468 A | 10/1999 | Hong et al. | 546/123 |
| 6,307,059 B1 | 10/2001 | Chang et al. | 548/531 |
| 2002/0032216 A1 | 3/2002 | Kim et al. | 514/300 |

FOREIGN PATENT DOCUMENTS

| EP | 0 058 614 A | 8/1982 |
|---|---|---|
| EP | 0 688 772 A | 12/1995 |
| EP | 0 805 156 A | 11/1997 |
| JP | 03 056479 A | 3/1991 |
| WO | WO 91 02526 A | 3/1991 |
| WO | WO 96 39406 A | 12/1996 |
| WO | WO 97 07098 A | 3/1997 |
| WO | WO 97 36874 A | 10/1997 |
| WO | WO 98 42705 A | 10/1998 |
| WO | WO 99 61420 A | 12/1999 |

OTHER PUBLICATIONS

Patent Abstracts of Japan, vol. 015, No. 202 (C–0834), May 23, 1991 (JP03056479A, Mar. 12, 1991).
G. Cormican, "Comparative Antimicrobial and Spectrum Activity of LB20304a, a New Fluoronated Naphthyridone Compound", *Abstracts of the 36th ICAAC*, 109 Abst F53 (1996).

J–H. Kwak, "Antimicrobial Activities of LB20304a, a New Quinolone Antibiotic", *The Journal of Applied Pharmacology* (4) pp. 378–384 (1996).

M–K. Seo, "Pharmacokinetics of LB20304, a New Fluoroquinolone, in Rats and Dogs", *Arch. Pharm. Res.* vol. 19, No. 5, pp. 359–367 (1996).

C. Yong Hong, et al., "Novel Fluoroquinolone Antibacterial Agents Containing Oxime–Substituted (Aminomethyl) pyrrolidines: Synthesis and Antibacterial Activity of 7–(4–Aminomethyl)–3–(methoxyimino) pyrrolidin–1–yl)–1–cyclopropyl–6–fluoro–4–oxo–1,4–dihydro [1,8] naphthyridine–3–carboxylic Acid (LB20304)", *J. Med. Chem,.* 40 (22) pp. 3584–3593 (1997).

M–K. Seo et al., "High Performance Liquid Chromatographic Assay of a New Fluoroquinone, LB20304, in the Plasma of Rats and Dogs", *Arch. Pharm. Res.* vol. 19, No. 6, pp .554–558 (1996).

M–J. Ahn, et al., "InVivo Efficacy of LB20304a, against Experimental Respiratory Tract Infection in Mice", *Yakhak Hoeji* vol. 40, No. 4, pp. 438–441 (1996).

M–J. Ahn, et al., "Effect of a New Fluoroquinolone LB20304a on Microflora of Caecum in Mice", *Yakhak Hoeji* vol. 40, No. 3, pp. 343–346 (1996).

M–J. Ahn, et al. "Post–Antibiotic Effect of LB20304, A New Quinolone Antibiotic", *Yakhak Hoeji* vol. 40, No. 3, pp. 347–350 (1996).

F. Marco, et al., Äntimicrobial Activity of LB20304, a Fluoronaphthyridone, Tested Against Anaerobic Bacteria, *J. Antimicrobial Chemother* vol. 40, No. 4, pp. 605–607 (1997).

Kelly et al., "Antipneumococcal Activity of SB 265805 (A New Broad Spectrum Quinolone) Compared with Nine Compounds by MIC," 38th ICAAC, San Diego CA, Abst F–87, p. 254 (1998).

U.S. application Ser. No. 09/381,491, filed Dec. 8, 1999, Salt of Naphthyridine Carboxylic Acid Derivative, Kim et al.

U.S. application Ser. No. 09/623,214, filed Aug. 30, 2000, Process for Preparing a Protected 4–Aminomethyl–Pyrrolidin–3–One, Chang et al.

*Primary Examiner*—Bernard Dentz
(74) *Attorney, Agent, or Firm*—Finnegan, Herderson, Farabrow, Garrett & Dunner, L.L.P.

(57) ABSTRACT

A process for the production of a naphthyridine carboxylic acid derivative having antibacterial activity.

21 Claims, 1 Drawing Sheet

Figure 1:
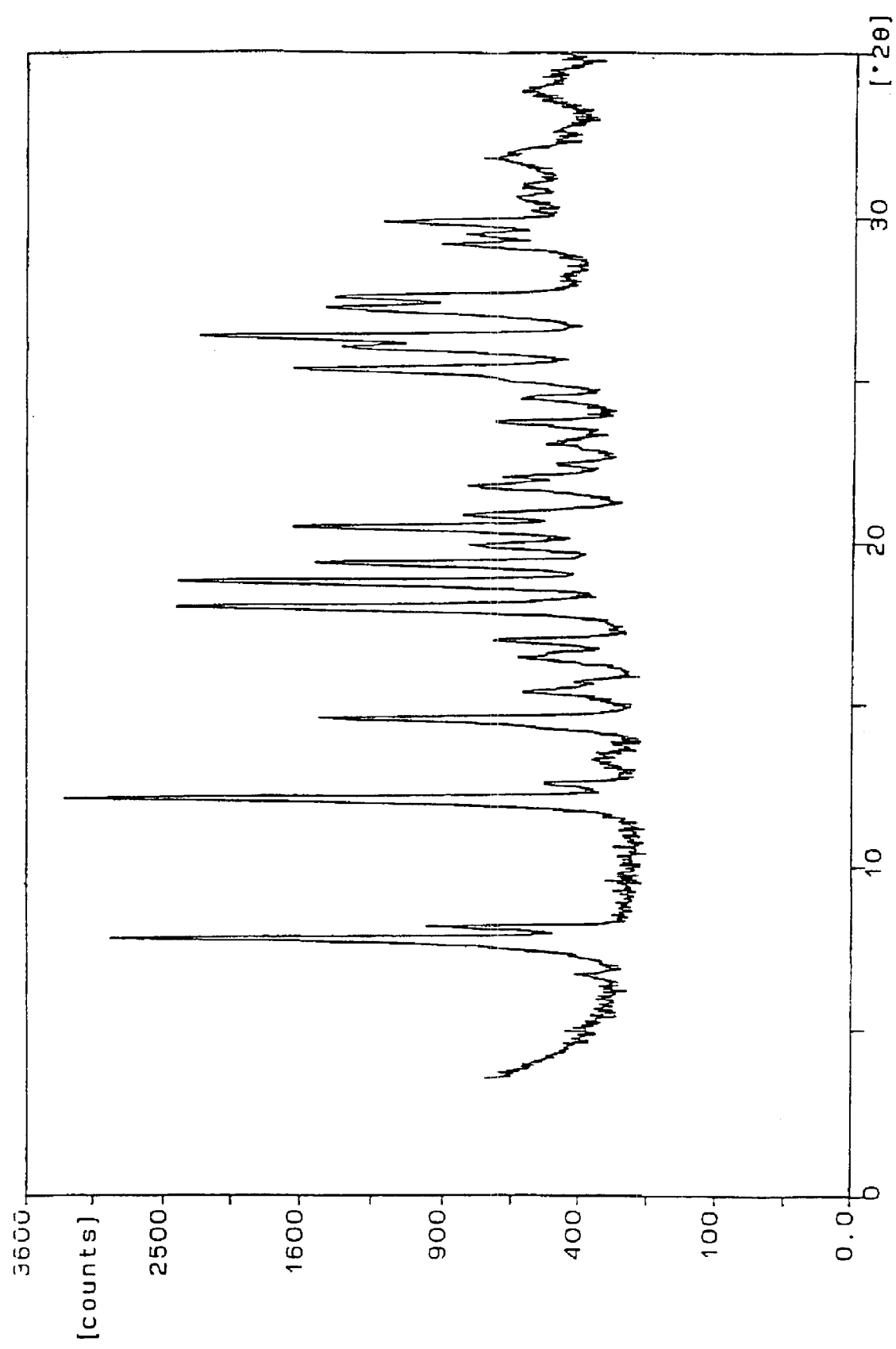

PROCESS FOR THE PRODUCTION OF A NAPHTHYRIDINE CARBOXYLIC ACID DERIVATIVE (METHANESULFONATE SESQUIHYDRATE)

This application is a 371 of PCT/EP99/07003 filed Sep. 15, 1999.

The present invention relates to a process for the production of a naphthyridine carboxylic acid derivative having antibacterial activity.

EP 688772 discloses novel naphthyridine carboxylic acid derivatives, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of formula I, having antibacterial activity.

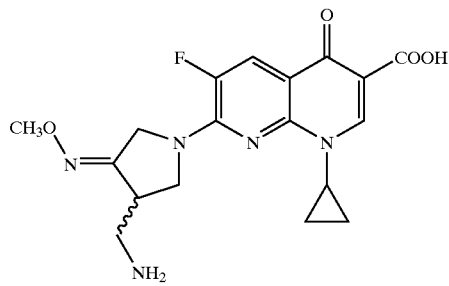

I

WO 98/42705 (published after the priority date of the present application) discloses (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate and hydrates thereof including the sesquihydrate (the "methanesulfonate sesquihydrate"). WO 98/42705 discloses a process for the production of the methanesulfonate sesquihydrate comprising reaction of the corresponding free base with methanesulfonic acid in dichloromethane/ethanol followed by recrystallisation of the resulting crude salt anhydrate from either water:acetone (10:7 v/v), or water:ethanol (1:2 v/v). The overall yield for this two step process is 70–80%. An alternative process for the production of the methanesulfonate sesquihydrate described in WO 98/42705 comprises exposing a solvate of the methanesulfonate (ethanol 0.11%) to high relative humidity (nitrogen>93% humidity).

The present invention relates to an improved process for the production of the methanesulfonate sesquihydrate which comprises direct salt and hydrate formation.

According to the invention there is provided a process for the production of 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate which comprises reacting 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid and methanesulfonic acid in a solvent comprising at least one water miscible cosolvent and water, and isolating the resulting solid product.

The 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (hereinafter referred to as "the free base") used in the process of the invention may be prepared as described in EP 688772.

Water miscible cosolvents which may be used in the process of the invention include $C_{1-8}$ alcohols, acetonitrile and dimethylformamide. The water miscible cosolvent is preferably a $C_{1-4}$ alcohol or a mixture thereof, e.g. methanol, ethanol and propanol; the preferred $C_{1-4}$ alcohol is isopropanol.

In addition to at least one water miscible cosolvent and water the solvent may contain other components, such as $C_{1-4}$ haloalkanes. However, the solvent preferably comprises essentially of a water miscible cosolvent and water.

Suitable ratios of water miscible cosolvent:water for use in the process of the invention include ratios in the range 10:1 to 1:2 v/v, preferred ratios are in the range 10:1 to 1:1 v/v, more preferably a ratio of water miscible cosolvent:water of 2:1 v/v is used.

Any suitable ratio of free base to solvent may be used, for example, a ratio of up to 1:100 w/v, particularly a ratio of about 1:9 w/v.

The process of the invention may suitably use from 0.7 to >3 mole equivalents of methanesulfonic acid, preferably 0.7 to 1.5 equivalents, more preferably 0.9 to 1.5 equivalents, especially about 1.0 equivalent of methanesulfonic acid (based on the free base).

The mixture of the free base and methanesulfonic acid may be warmed in the solvent to aid dissolution. On cooling the methanesulfonate sesquihydrate will crystallise out of solution. To aid crystallisation the solution may be seeded with a small quantity of solid methanesulfonate sesquihydrate. In order to obtain polymorphically pure methanesulfonate sesquihydrate it is preferable that seeding of the solution is completed before crystallisation begins. Seeding of the crystallisation solution is preferably performed at a temperature $\geq 25°$ C., for example at a temperature of about 30° C.

The process of the invention may be used to produce racemic methanesulfonate sesquihydrate or may be used for the production of enantiomerically enriched or enantiomerically pure methanesulfonate sesquihydrate, using racemic or enantiomerically enriched or enantiomerically pure free base. Enantiomerically enriched or enantiomerically pure free base may be prepared by resolution of the racemic free base, e.g. by chiral HPLC.

The process according to the invention has the advantage that direct salt formation eliminates one step in the synthesis and gives a high yield of high purity methanesulfonate sesquihydrate. In turn these advantages result in improved throughput and savings in labour and materials costs during manufacture.

All publications, including but not limited to patents and patent applications, cited in this specification are herein incorporated by reference as if each individual publication were specifically and individually indicated to be incorporated by reference herein as though fully set forth.

The invention is illustrated by the following example. However, it should be understood that the example is intended to illustrate but not in any manner limit the scope of the invention.

EXAMPLE 1

Preparation of the Methanesulfonate Sesquihydrate

To a suspension of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (20.00 g, 51.4 mmol) in isopropanol (120 ml) and water (60 ml) was added methanesulfonic acid (3.300 ml, 50.9 mmol) at 38–40° C. The resultant dark brown solution was stirred for 15 min after which time charcoal (6.00 g of Darco G-60) was added. The suspension was stirred at 38–40° C. for 4 h then filtered. The filtrate was allows to cool to 30° C. and seed crystals of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate (15 mg) added. A precipitate began to form within 15 min. The suspension was allowed to cool to 20–23° C. over 90 min and was stirred for 36 h. The slurry was cooled to 0–5° C. for 60 min then filtered and washed with isopropanol (50 ml and 44 ml). The product was sucked dry for 30 min and then further dried at 50–55° C. under vacuum. The dried product was exposed to the atmosphere for 18 h to give the methanesulfonate sesquihydrate 21.29 g (85%), purity>99.5% by HPLC.

The X-ray diffraction pattern of the methanesulfonate sesquihydrate was measured as follows:

| | |
|---|---|
| Diffractometer type: | PW1710 BASED |
| Tube anode: | Cu |
| Generator tension [kV]: | 40 |
| Generator current [mA]: | 30 |
| Wavelength Alpha1 [A]: | 1.54060 |
| Wavelength Alpha2 [A]: | 1.54439 |
| Intensity ratio (alpha1/alpha2): | 0.500 |
| Divergence slit: | AUTOMATIC |
| Irradiated length [mm]: | 12 |
| Receiving slit: | 0.1 |
| Spinner: | ON |
| Monochromator used: | YES |
| Start angle [°2θ]: | 3.500 |
| End angle [°2θ]: | 35.000 |
| Step size [°2θ]: | 0.020 |
| Maximum intensity: | 2970.250 |
| Time per step [s]: | 2.300 |
| Type of scan: | STEP |
| Minimum peak tip width: | 0.10 |
| Maximum peak tip width: | 1.00 |
| Peak base width: | 2.00 |
| Minimum significance: | 0.50 |

The X-ray diffraction pattern of the methanesulfonate sesquihydrate is shown in FIG. 1. The compound shows characteristic peaks at 2θ=8.2, 12.2 and 14.6°.

What is claimed is:

1. A process for the production of 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate which comprises: (a) forming a crystallization solution comprising 7-(3-aminomethyl-4-methoxyiminopyrrolidin-1-yl)-1-cyclopropyl-6-fluoro-4-oxo-1,4-dihydro-1,8-naphthyridine-3-carboxylic acid, methanesulfonic acid, and a solvent comprising at least one least one water miscible cosolvent and water, wherein the ratio of water miscible cosolvent:water is in the range of 2:1 to 1:2 v/v, (b) reacting said carboxylic acid and methanesulfonic acid in the solvent, and (c) isolating the resulting solid product which comprises 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate.

2. A process according to claim 1 wherein the water miscible cosolvent is a $C_{1-4}$ alcohol.

3. A process according to claim 2 wherein the water miscible cosolvent is isopropanol.

4. A process according to claim 1 wherein the ratio of water miscible cosolvent:water is 2:1 v/v.

5. A process according to claim 1 wherein the ratio of 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid:solvent is 1:100 w/v or more.

6. A process according claim 1 which uses from 0.7 to 1.5 mole equivalents of methanesulfonic acid.

7. A process according to claim 1 wherein the crystallization solution is seeded with 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate to aid crystallization.

8. A process according to claim 7 wherein the solution is seeded whilst at a temperature of ≧25° C.

9. A process according to claim 8 wherein the solution is seeded whilst at a temperature of about 30° C.

10. A process for the production of 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate which comprises:

(a) forming a crystallization solution comprising 7-(3-aminomethyl-4-methoxyiminopyrrolidin-1-yl)-1-cyclopropyl-6-fluoro-4-oxo-1,4-dihydro-1,8-naphthyridine-3-carboxylic acid, methanesulfonic acid, and a solvent comprising at least one least one $C_{1-4}$ alcohol and water, wherein the ratio of $C_{1-4}$ alcohol:water is in the range of 2:1 to 1:2 v/v, the ratio of said carboxylic acid to said solvent is 1:100 w/v or more, and from 0.7 to 1.5 mole equivalents of the methanesulfonic acid is used, (b) reacting said carboxylic acid and methanesulfonic acid in the solvent, and (c) isolating the resulting solid product which comprises 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate.

11. A process according to claim 10 wherein the $C_{1-4}$ alcohol is isopropanol.

12. A process according to claim 10 wherein the ratio of $C_{1-4}$ alcohol:water is 2:1 v/v.

13. A process according to claim 10 wherein the crystallization solution is seeded with 7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate to aid crystallization.

14. A process according to claim 13 wherein the solution is seeded whilst at a temperature of ≧25° C.

15. A process according to claim 13 wherein the solution is seeded whilst at a temperature of about 30° C.

16. A process according to claim 1 wherein the methanesulfonate sesquihydrate is crystallized out of solution by cooling.

17. A process according to claim 1 wherein the resulting solid product is dried.

18. A process according to claim 1 wherein the resulting solid product is dried at 50–55° C. under vacuum.

19. A process according to claim 10 wherein the methanesulfonate sesquihydrate is crystallized out of solution by cooling.

20. A process according to claim 10 wherein the resulting solid product is dried.

21. A process according to claim 10 wherein the resulting solid product is dried at 50–55° C. under vacuum.

* * * * *

UNITED STATES PATENT AND TRADEMARK OFFICE
CERTIFICATE OF CORRECTION

PATENT NO. : 6,818,771 B1
DATED : November 16, 2004
INVENTOR(S) : Hayes et al.

It is certified that error appears in the above-identified patent and that said Letters Patent is hereby corrected as shown below:

Title page,
Item [74], *Attorney, Agent or Firm*, "Finnegan, Herderson, Farabrow, Garrett & Dunner, L.L.P." should read -- Finnegan, Henderson, Farabrow, Garrett & Dunner, L.L.P. --.

Column 3,
Line 48, delete "least one".

Column 4,
Line 3, "according claim" should read -- according to claim --.
Line 23, delete the second occurrence of "least one".
Lines 24-25, "alcohol- :" should read -- alcohol : --.

Signed and Sealed this

Fifteenth Day of March, 2005

JON W. DUDAS
*Director of the United States Patent and Trademark Office*